US00PP31220P2

(12) United States Plant Patent
Tristram

(10) Patent No.: US PP31,220 P2
(45) Date of Patent: Dec. 10, 2019

(54) ***GAURA* PLANT NAMED 'WALSILFOU'**

(50) Latin Name: *Gaura lindheimeri*
Varietal Denomination: Walsilfou

(71) Applicant: Walberton Plants Ltd., Walberton (GB)

(72) Inventor: David R. Tristram, Arundel (GB)

(73) Assignee: Walberton Plants Ltd., Walberton (GB)

( * ) Notice: Subject to any disclaimer, the term of this patent is extended or adjusted under 35 U.S.C. 154(b) by 0 days.

(21) Appl. No.: 16/501,317

(22) Filed: Mar. 25, 2019

(51) Int. Cl.
*A01H 5/02* (2018.01)
*A01H 6/00* (2018.01)

(52) U.S. Cl.
USPC ..... Plt./432

(58) Field of Classification Search
USPC ..... Plt./263.1, 432
See application file for complete search history.

*Primary Examiner* — Susan McCormick Ewoldt
*Assistant Examiner* — Karen M Redden
(74) *Attorney, Agent, or Firm* — Barbara Campbell; James M. Weatherly; Cochran Freund & Young LLC

(57) ABSTRACT

A new cultivar of *Gaura* named 'Walsilfou' that is characterized by dense compact habit throughout the season, variegated cream-green foliage and single sterile flowers which open light pink in color becoming pure white in color when fully open.

2 Drawing Sheets

Figure 1:
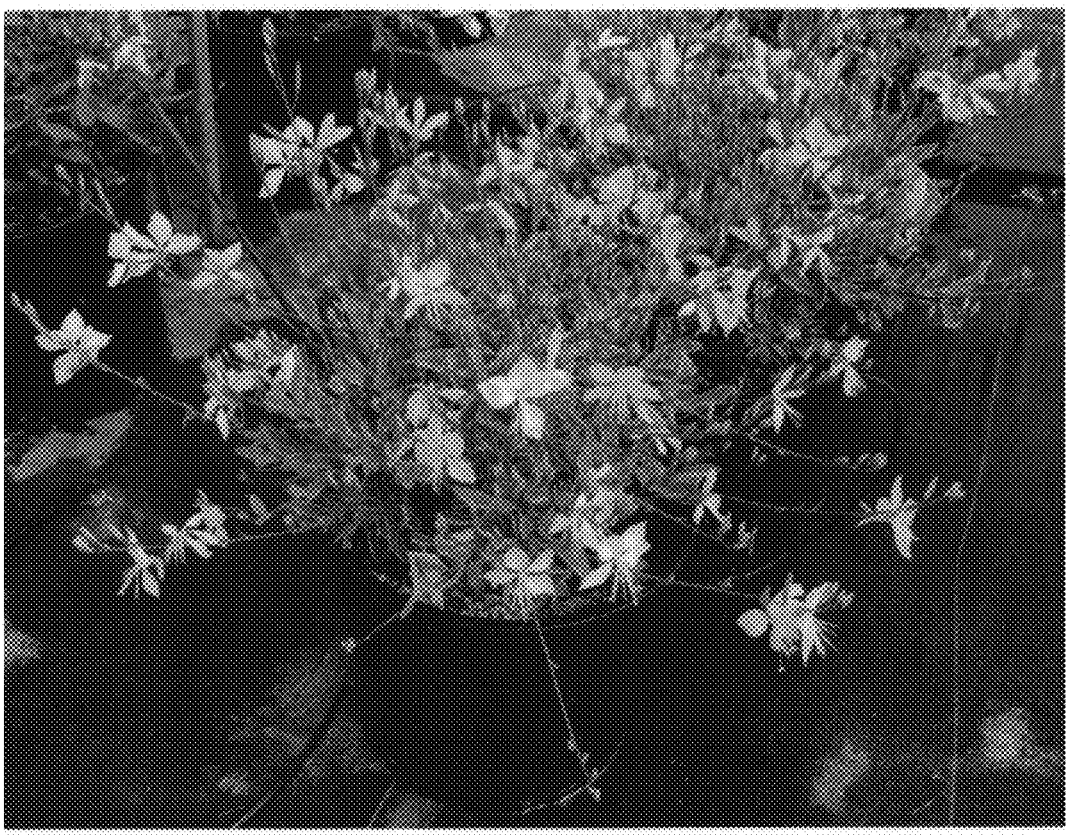

Genus and species: *Gaura lindheimeri.*
Variety denomination: 'Walsilfou'.

BACKGROUND OF THE NEW PLANT

The present invention relates to a new and distinct variety of butterfly bush grown for use as an ornamental plant in planted containers, garden borders, and for mass landscape planting. The new cultivar is known botanically as *Gaura lindheimeri* and will be referred to hereinafter by the cultivar name 'Walsilfou'.

In spring 2015, the inventor observed within a growing crop of his white-flowered variety of *Gaura* Plant Named 'Walsnofou' (U.S. Plant Pat. No. 19,376) a naturally occurring whole plant mutation which exhibited gold-yellow and green variegated foliage. The growing crop was in production out-of-doors at the inventor's nursery in Arundel, West Sussex, United Kingdom. The inventor removed this gold-yellow and green mutated plant for further evaluation.

In summer 2015, the inventor observed that one branch of the gold-yellow and green variegated plant mutation exhibited a contrasting cream and green variegation. The inventor successfully rooted and established plants from vegetative stem cuttings taken from the cream and green variegated branch. The inventor has established that the discovered sport, 'Walsilfou' reproduces true to type in successive generations of asexual reproduction, without any reversion either to the gold-yellow variegation of its immediate sport parent, or to the all green foliage of the original parent 'Walsnofou'.

All propagations have been carried out in an unheated greenhouse at the inventor's nursery in Arundel, United Kingdom using the method of stem cuttings. The inventor has confirmed that 'Walsilfou' is stable and reproduces true to type in successive generations of asexual reproduction.

SUMMARY

The following traits have been repeatedly observed and represent the distinguishing characteristics of 'Walsilfou'.

'Walsilfou' has not been tested under all possible conditions and phenotypic differences may be observed with variations in environmental, climatic, and cultural conditions, without however, any variance in genotype.

1. 'Walsilfou' exhibits dense compact habit which is maintained throughout the season.
2. 'Walsilfou' exhibits variegated cream-green foliage.
3. 'Walsilfou' bears sterile white flowers continuously from spring until fall.
4. 'Walsilfou' is hardy in USDA Zone 5.
5. Excluding its flowers, 'Walsilfou' reaches 30 cm in height and 30 cm in width after 12 months in a 1 gallon container.
6. Excluding its flowers, 'Walsilfou' reaches 35 cm in height and 40 cm in width at maturity when planted in the landscape.

BRIEF DESCRIPTION OF THE PHOTOGRAPHS

The accompanying color photographs illustrate the overall appearance of 'Walsilfou' showing the colors as true as it is reasonably possible to obtain in colored reproductions of this type. Colors in the drawing may differ from the color values cited in the detailed botanical description, which accurately describe the actual colors of the new variety 'Walsilfou'.

FIG. 1 depicts an individual plant of 'Walsilfou' in full bloom. The illustrated plant is one year old and is growing in a 2 gallon pot outdoors in Oxnard, Calif. The drawing has been made from a photograph taken in mid-July in Oxnard, Calif. No growth regulators have been used.

Figure 2:
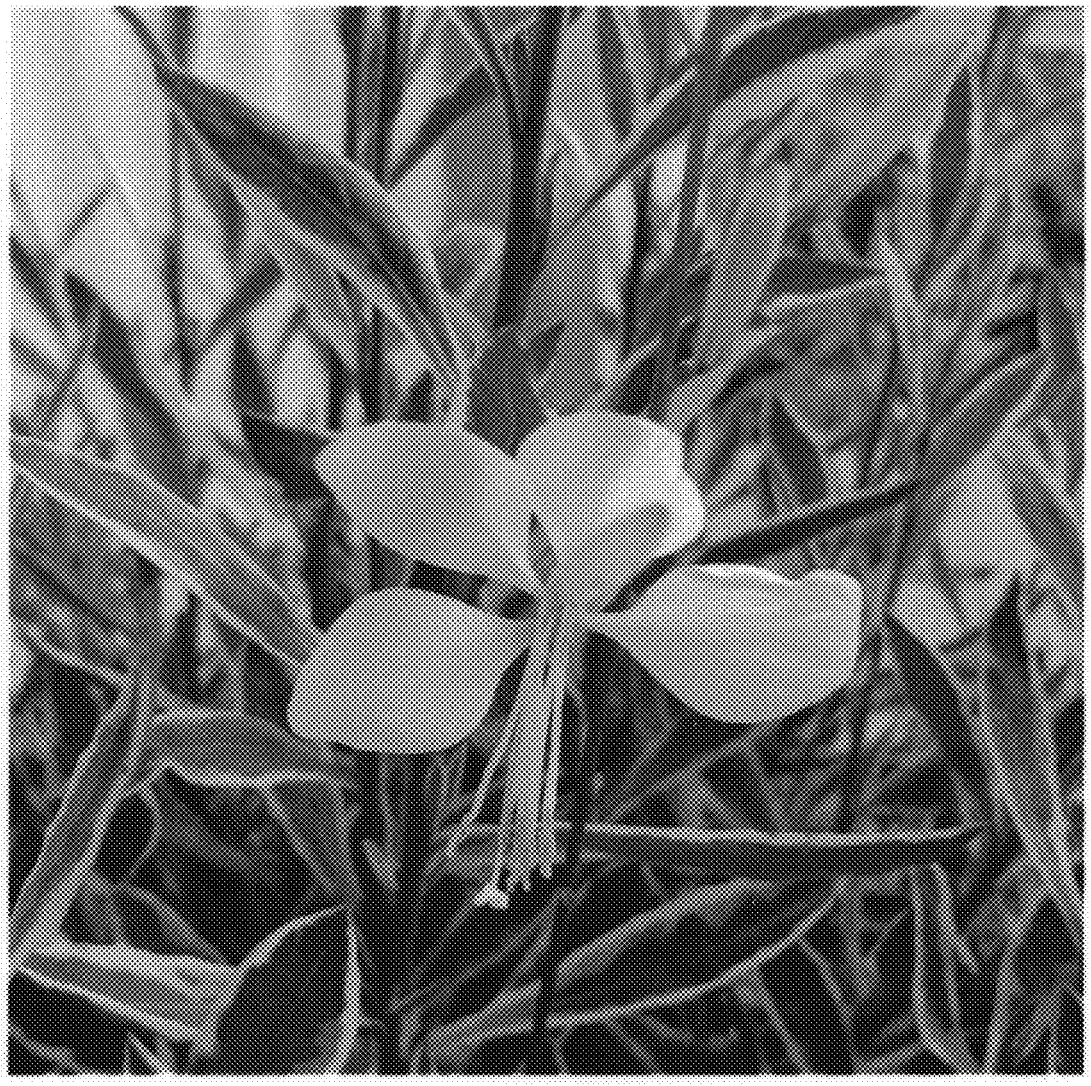

FIG. 2 presents a close-up view of a single flower of 'Walsilfou' when fully open.

BOTANICAL DESCRIPTION OF THE PLANT

The following is a detailed botanical description of the new *Gaura* variety named 'Walsilfou'. Data was collected in Oxnard, Calif. in mid-July of 2018 from 12-month-old plants that were grown in 2 gallon containers outdoors in full sun. The growing requirements are similar to other *Gaura*. Color determinations were made in accordance with The 2007 Royal Horticultural Society Colour Chart from London England, except where general color terms of ordinary dictionary significance are used.

Classification:

*Family*.—Onagraceae.

*Genus*.—*Gaura*.

*Species*.—*Lindheimeri*.

*Common name*.—*Gaura*, Beeblossom.

Parentage: Second generation mutation sport of 'Walsnofou' (U.S. Plant Pat. No. 19,376).

Plant:

*Commercial classification*.—Perennial.

*Use*.—Ornamental plant for containers, garden borders and planting in the landscape.

*Special cultural requirements*.—None.

*Susceptibility to pests and disease*.—None.

*Root system*.—Fine and fibrous.

*Drought tolerance*.—Drought tolerant once established in the landscape.

*Bloom period*.—Continuously from late spring until fall.

*Habit*.—Dense compact habit.

*Dimensions* (*excluding inflorescences*).—30 cm in height and 30 cm in width.

*Hardiness*.—USDA Zone 5.

*Propagation*.—Stem cuttings.

*Time to develop roots*.—2 to 3 weeks from initial cutting.

*Crop time*.—6 weeks are required to produce a 3 cm to 5 cm starter plant from insertion of an unrooted cutting. A further 10 to 12 weeks are required to produce a flowering plant after potting into a 1 or 2 gallon container.

Stems:

*Shape*.—Cylindrical.

*Color*.—Emerges 139C becoming 182B at maturity.

*Texture*.—Stiff.

*Dimensions*.—20 cm to 25 cm in length and 3 mm in diameter.

*Surface*.—Pubescent.

*Internode length* (*average*).—0.50 cm.

Leaves:

*Arrangement*.—Alternate.

*Shape*.—Oblanceolate.

*Division*.—Simple.

*Apex*.—Acute.

*Base*.—Attenuate.

*Venation pattern*.—Pinnate, midrib depressed on adaxial surface, raised on abaxial surface.

*Vein color* (*both surfaces*).—139D.

*Margins*.—Entire.

*Attachment*.—Sessile.

*Leaf surface* (*both surfaces*).—Puberulent.

*Leaf appearance*.—Young leaves glossy, otherwise matte.

*Leaf length* (*average*).—5 cm.

*Leaf width* (*average*).—1 cm.

*Leaf color* (*adaxial surface*).—Predominantly 143C with some areas N138C towards margin.

*Leaf color* (*abaxial surface*).—N138B and N138C both present.

*Leaf margin variegation* (*both surfaces*).—10A on younger leaves becoming 10C or 10D as leaf ages. Variegation extends approximately 1.0 mm to 1.5 mm from margin edge.

*Fragrance*.—None observed.

Inflorescence:

*Inflorescence*.—Terminal raceme consisting of single flowers.

*Flower quantity per inflorescence*.—In any one day, 1 or 2 flowers are freshly open, and each raceme bears approximately 20 flowers over time.

*Flower quantity per plant*.—Approximately 50 freshly open flowers per day.

*Lastingness of flower*.—Fully open for 1 to 2 days.

*Flower depth*.—1.5 cm.

*Flower diameter*.—3.75 cm. Flower color (petals, sepals) are colored light pink, ranging between 65D and 65B, at bud emergence, becoming pure white, NN155D, when fully open.

*Flower shape*.—Clawed after bud emergence, opening flat.

*Flowers persistence*.—Persistent for 1 to 2 days after open flowering, then self-cleaning.

*Aspect*.—Facing outward.

Flower bud:

*Bud dimensions*.—1.5 cm in length and 4 mm in diameter.

*Bud arrangement*.—Buds are produced at the apex of the raceme, arranged in clusters of 5 to 7 buds.

*Bud shape*.—Cylindrical.

*Bud color*.—At emergence, 160C, then becoming 50B at apex and base, and then 50B throughout (immediately prior to petal emergence).

*Bud surface*.—Pubescent.

*Bud apex*.—Acute.

*Bud base*.—Truncate.

Corolla:

*Petals*.—Four in number, fan-like arrangement.

*Petal shape*.—Obovate.

*Petal color* (*adaxial and abaxial surfaces*).—65D and 65B at bud emergence, becoming pure white, NN155D, when fully open.

*Petal dimensions*.—2 cm in length and 1 cm in width.

*Petals fused or unfused*.—Unfused.

*Petal margin*.—Entire.

*Petal apex*.—Broadly acute.

*Petal base*.—Attenuated.

*Petal surfaces* (*adaxial and abaxial*).—Glabrous.

Calyx:

*Calyx*.—Tubular, lightly pubescent.

*Sepals*.—4, reflexed.

*Sepals fused or unfused*.—Unfused.

*Sepal color*.—N66B at emergence, becoming pale pink N155B.

*Sepal dimensions*.—1.5 cm in length and 1.5 mm to 2.0 mm in width.

*Sepal surface*.—Puberulent.

Pedicel:

*Pedicel dimensions*.—0.50 cm in length and 1.50 mm in width.

*Pedicel color*.—146D initially, quickly becoming 178A.

*Pedicel shape*.—Cylindrical.

*Pedicel surface*.—Glabrous.

Peduncle:

*Peduncle dimensions*.—20 cm to 30 cm in length and 2 mm to 3 mm in diameter.

*Peduncle shape*.—Cylindrical.

*Peduncle color*.—144A.

*Peduncle surface*.—Glabrous.

*Flower fragrance*.—None observed.

Reproductive organs:

*Stamens*.—Eight in number.

*Stamen color*.—NN155D.

*Stamen length* (*average*).—2.10 cm.

*Anther length*.—3 mm.

*Anther color*.—199A.

*Pollen color*.—163C.

*Pollen quantity*.—Moderate.

*Pistil*.—One in number.

*Pistil length*.—2 cm.

*Pistil color*.—155B.

*Pistil shape*.—Filament.

*Stigma shape*.—4-lobed.

*Stigma color*.—NN155D.

*Stigma width*.—3 mm.

*Ovary position*.—Inferior.

*Ovary color*.—138D.

*Ovary shape*.—Ovoid.

*Ovary dimensions*.—3 mm in height and 2 mm in width.

Seed: No seed observed to date.

COMPARISON WITH PARENTAL LINES AND KNOWN VARIETY

'Walsilfou' may be compared with its original sport parent 'Walsnofou' as follows. Whereas 'Walsnofou' bears entirely green foliage without any variegation, the foliage of 'Walsilfou' is green with cream-colored marginal variegation.

The closest variety of *Gaura* known to the inventor is the variegated variety 'Corrie's Gold' (unpatented) which also bears white flowers. In comparison with 'Walsilfou', 'Corrie's Gold' has a more open and spreading habit. 'Corrie's Gold' achieves 90 cm in height and 70 cm in width.

I claim:

1. A new and distinct cultivar of *Gaura* plant named 'Walsilfou', as described and illustrated herein.

* * * * *